United States Patent [19]
Zobitne et al.

[11] Patent Number: 5,998,484
[45] Date of Patent: Dec. 7, 1999

[54] INSECTICIDAL COMPOSITIONS AND METHOD OF CONTROLLING INSECT PESTS USING SAME

[75] Inventors: Karen A. Zobitne, Middletown; Michael J. Gehret, Lititz, both of Pa.

[73] Assignee: Woodstream Corporation, Lititz, Pa.

[21] Appl. No.: 09/060,141

[22] Filed: Apr. 15, 1998

[51] Int. Cl.$^6$ .......................... A01N 65/00; A01N 41/02; A01N 61/02; A01N 25/06

[52] U.S. Cl. .......................... 514/711; 514/729; 514/762; 514/763; 514/768; 514/772; 514/975; 424/195.1; 424/43; 424/45

[58] Field of Search .......................... 514/711, 729, 514/762, 763, 768, 772, 975; 424/195.1, 43, 45

[56] References Cited

U.S. PATENT DOCUMENTS

| | | | |
|---|---|---|---|
| 351,897 | 11/1886 | Boyer | 424/416 |
| 1,630,836 | 5/1927 | Drushel | 424/701 |
| 2,898,267 | 8/1959 | Lindner | 514/568 |
| 3,321,364 | 5/1967 | Kessler | 424/195.1 |
| 3,887,710 | 6/1975 | Shaver et al. | 514/479 |
| 4,000,266 | 12/1976 | Incho | 514/461 |
| 4,164,561 | 8/1979 | Hautmann | 424/416 |
| 4,193,986 | 3/1980 | Cox | 424/411 |
| 4,195,080 | 3/1980 | Herrera et al. | 424/195.1 |
| 4,587,123 | 5/1986 | Price | 424/195.1 |
| 4,627,850 | 12/1986 | Deters et al. | 604/892.1 |
| 4,637,830 | 1/1987 | Dyer et al. | 504/141 |
| 4,671,960 | 6/1987 | Thielen et al. | 424/195.1 |
| 4,735,358 | 4/1988 | Morita et al. | 239/1 |
| 4,767,882 | 8/1988 | Suzukamo et al. | 560/100 |
| 4,874,610 | 10/1989 | Cousin | 424/196.1 |
| 4,891,222 | 1/1990 | Eichhoefer | 424/196.1 |
| 4,933,181 | 6/1990 | Brown et al. | 424/405 |
| 4,933,371 | 6/1990 | Hink et al. | 514/739 |
| 5,079,000 | 1/1992 | Takahashi et al. | 424/195.1 |
| 5,104,658 | 4/1992 | Hagarty | 424/405 |
| 5,106,622 | 4/1992 | Sherwood et al. | 424/195.1 |
| 5,110,594 | 5/1992 | Morita | 424/405 |
| 5,118,506 | 6/1992 | Eichoefer | 424/196.1 |
| 5,149,521 | 9/1992 | Hirose et al. | 424/58 |
| 5,208,029 | 5/1993 | Plummer et al. | 424/405 |
| 5,216,009 | 6/1993 | Fujimoto et al. | 514/406 |
| 5,240,708 | 8/1993 | Plummer et al. | 424/405 |
| 5,242,907 | 9/1993 | Dawson | 514/65 |
| 5,273,953 | 12/1993 | Szekely et al. | 504/116 |
| 5,288,632 | 2/1994 | Pannell | 435/243 |
| 5,346,704 | 9/1994 | Lajoie | 424/717 |
| 5,372,817 | 12/1994 | Locke et al. | 424/405 |
| 5,449,517 | 9/1995 | Fitzjarrell | 424/195.1 |
| 5,489,433 | 2/1996 | Aboud | 424/405 |
| 5,518,736 | 5/1996 | Magdassi et al. | 424/451 |
| 5,547,918 | 8/1996 | Newton et al. | 504/116 |
| 5,556,881 | 9/1996 | Gran Marisi | 514/557 |
| 5,569,411 | 10/1996 | Steltenkamp et al. | 510/383 |
| 5,658,954 | 8/1997 | Targosz | 514/617 |
| 5,681,859 | 10/1997 | James et al. | 514/625 |

FOREIGN PATENT DOCUMENTS 629345   12/1994   European Pat. Off. .

OTHER PUBLICATIONS

Derwent Abstract, Accession No. 1995—024010, abstracting EP 629345 (1994).
Abstract—Indian Journal of Agronomy 38(3):443–448 (1993).
Abstract—Journal of the Indian Society of Soil Science 41(1):176–177 (1993).
Abstract—Int'l. Journal of Food Sciences and Nutrition, 46(3):225–228 (1995).
Abstract—Plant Foods for Human Nutrition (Dordrect), 47(2)109–114 (1995).
Abstract—Journal of Advanced Zoology 16(2): 85–87 (1995).
Abstract—Fertilizer Research 44(1):17–21 (1995).

*Primary Examiner*—John Pak
*Attorney, Agent, or Firm*—Jacobson, Price, Holman & Stern, PLLC

[57] ABSTRACT

A highly effective, broad spectrum, quick-acting, nonpoisonous insecticidal composition with synergistic kill ratio and kill time is provided when cornmint oil and sodium lauryl sulfate are combined as the essential active ingredients.

11 Claims, 2 Drawing Sheets

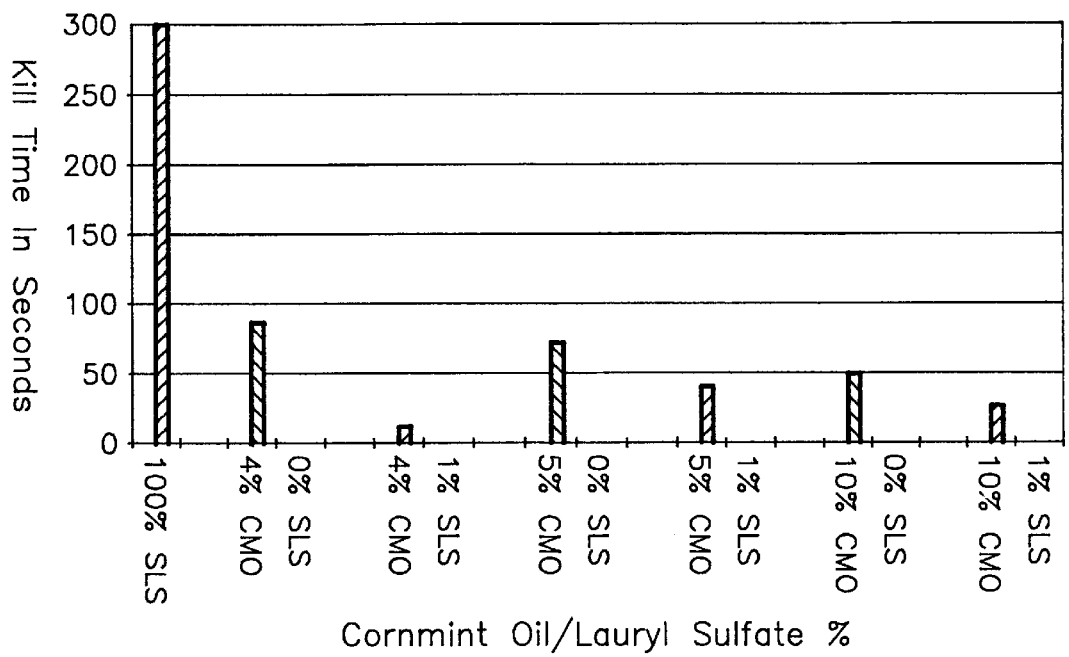

INSECTICIDAL COMPOSITIONS AND METHOD OF CONTROLLING INSECT PESTS USING SAME

BACKGROUND OF THE INVENTION

This Invention relates to insecticidal compositions and methods of using same to control various crawling and flying insect pests, and relates more particularly to synergistic "poison-free" insecticides adapted to unexpectedly increase insect mortality and reduce kill time.

Commercially available insecticides, including those available for home use, commonly comprise active ingredients or "poisons" which are not only toxic to the target insect pests, but, if used in relatively confined environments and delivered as aerosol sprays, can be present in sufficient concentration to also be toxic to humans and household pets. Various undesirable side effects may include immediate or delayed neurotoxic reactions, and/or suffocation. Even the noxious odor of such materials can cause headaches or upset stomachs in some individuals. These adverse side effects are exacerbated when such compositions come in contact with persons of increased sensitivity, or persons of small body mass such as children or babies.

For some time, efforts have been made to develop insecticidal compositions, particularly those intended for residential use in aerosol form, which are effective in killing the targeted insect pests completely and quickly, but non-toxic to humans and pets. The Environmental Protection Agency (EPA) regulates the use of potentially toxic ingredients in pesticidal compositions under the Federal Insecticide, Fungicide and Rodenticide Act. Certain materials have been deregulated by the EPA or otherwise identified as acceptable "safe" substances offering minimum risk in normal use. Such substances are generally considered "poison-free" by the consumer. Thus, the term "poison-free" or "nonpoisonous" as used herein is intended to convey a composition that, while highly effective in killing targeted insect pests, is safe to use around humans, particularly small children, and pets.

Unfortunately, "poison-free" insecticidal compositions available heretofore incorporating deregulated materials as the active ingredient have had limited efficacy. Attempts to use deregulated essential oils as the active ingredient in such insecticides, while having limited success, have generally been found to be either cost prohibitive, inadequately lethal to control a range of targeted insect pest species, or too slow-acting to enable the user to confirm that the insect has been killed and to dispose of the dead insect so as to avoid polluting the environment.

Among the insects which are found to be particularly undesirable are cockroaches, both the American and German species. These pests shed their "skin" which, over time, disintegrates forming what is known as "cuticle" in the air, a particular problem for people suffering from asthma. Thus, not only is it important to kill cockroaches with an effective insecticide, the kill time must be sufficiently short for the carcass to be properly disposed of before the insect can crawl into a remote area to die.

While cockroaches are a prime target for a household spray, for general application such materials must also be effective against other crawling insects, such as ants, water bugs, silverfish, crickets, spiders and centipedes. Additionally, aerosol compositions of such insecticides of proper concentration must also be effective against various flying insects, including flies, mosquitoes, gnats, moths, wasps, hornets, yellow jackets and other bees, both inside and outside of the house.

Among the materials exempted by the EPA is cornmint oil (also known as Japanese mint or *Mentha arvensis*). Cornmint oil includes a high concentration of menthol and is known to contain alpha-pinene, myrcene, limonene, gamma-terpenine, 3-octanol, menthofuran, beta-caroyophyllene, germa-crene D and beta-pinene, along with other components. As with other mint oils, cornmint oil has been used as a flavorant in mouthwashes, cough syrups, throat lozenges, chewing gum, and the like.

While cornmint oil has been considered, along with many other essential oils, for its insecticidal or insect repellent properties, it has not been shown to be particularly effective, and certainly has not been distinguished from other materials of this kind as a candidate for special attention.

SUMMARY OF THE INVENTION

It is a primary object of the instant invention to provide a "poison-free" broad-spectrum insecticide containing, as an essential active ingredient, materials that have been approved by the EPA as safe or as offering minimum risk in products of this nature.

Yet another object of this invention is the provision of an aerosol insecticide which is not detrimental to the health of humans or pets and which is environmentally safe, yet effective in killing substantially all targeted insect pests with which it comes in contact.

Another object of the instant invention is the provision of an insecticidal composition that not only effectively kills 100% of the insects with which it comes in contact, but kills such insects within seconds of contact so that the user can be certain of the effectiveness of the insecticide, and the insect carcass can be safely and easily disposed of without contaminating the environment.

Yet a further object of this invention is the provision of an insecticidal composition comprising a combination of essential active ingredients which, individually are relatively ineffective, but act in concert to provide high total killing power with a substantially decreased kill time.

A further object of this invention is the provision of a pesticide comprising cornmint oil, the insecticidal activity of which has been synergistically enhanced by the incorporation of effective quantities of sodium lauryl sulfate, so as to surprisingly improve both the kill ratio and kill time, providing greater insecticidal activity than either of the ingredients and more effective and faster-acting killing power than would be expected by combining these components.

Yet another object of the invention is the provision of a "poison-free", highly effective insecticidal composition, which may be sprayed in aerosol form from a standard pump dispenser or, which may incorporate a propellant such as carbon dioxide ($CO_2$) or the like in a pressurized container of conventional design, so that the composition may be sprayed directly onto a crawling or flying insect pest.

Another object of this invention is the provision of an insecticidal composition of the type described incorporating mineral oil or other such material to retain the essential active ingredients on a contacted surface for residual killing power over an extended period of time.

Another object of this invention is the provision of an insecticide which can be provided in aerosol form, and which has a fresh mint scent.

These and other objects of the invention, as well as many of the attendant advantages thereof, will become more readily apparent when reference is made to the following detailed description of the preferred embodiments which refers to the accompanying drawings.

BRIEF DESCRIPTION OF THE DRAWINGS

FIG. 3 is a bar graph illustrating the insecticidal effects of combining cornmint oil with sodium lauryl sulfate in killing black ants.

DETAILED DESCRIPTION OF THE PREFERRED EMBODIMENTS

Figure 1:
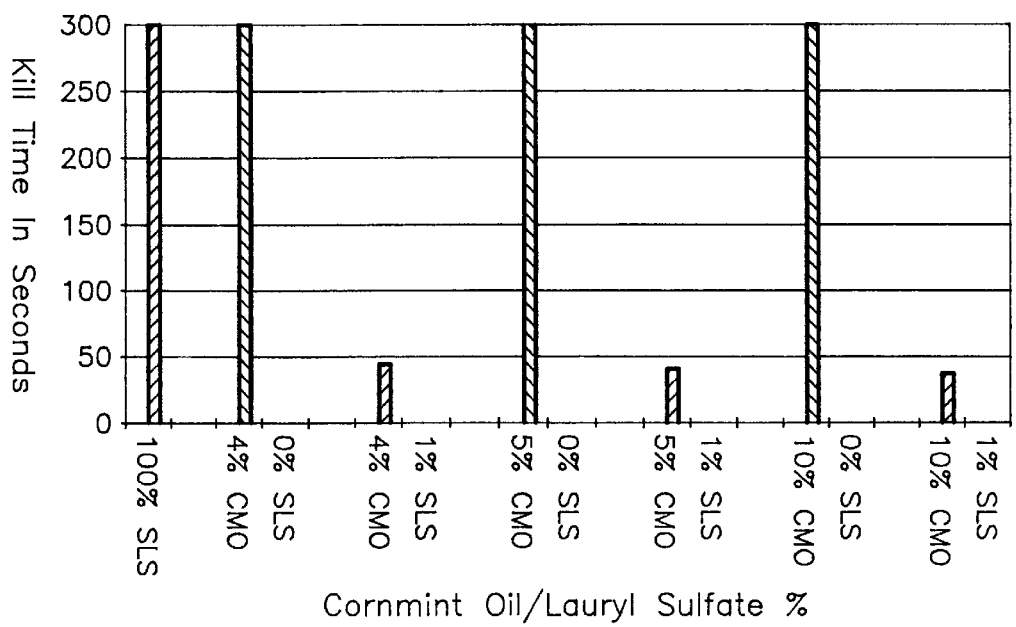
FIG. 1 is a bar graph illustrating the insecticidal effects of combining cornmint oil with sodium lauryl sulfate in killing American cockroaches.

In describing a preferred embodiment of the invention specific terminology will be resorted to for the sake of clarity. However, the invention is not intended to be limited to the specific terms so selected, and it is to be understood that each specific term includes all technical equivalents which operate in a similar manner to accomplish a similar purpose.

The essential active ingredients in the insecticidal composition of the instant invention comprise a combination, in synergistic proportions, of cornmint oil and sodium lauryl sulfate. The active ingredients may be dissolved in an inert carrier such as water and dispensed in a conventional manner, e.g., from a standard pump-spray container. Alternatively, and preferably, the aqueous insecticidal composition may be packaged in a pressurized container such as a conventional aerosol can or the like, utilizing an expandable gas, such as carbon dioxide ($CO_2$) as a propellant in a well known manner.

For optimum effectiveness, the insecticidal composition of this invention is sprayed directly on crawling or flying insect pests in sufficient concentrations to cause death within seconds. A material such as mineral oil may be incorporated into the composition to provide residual killing power on surfaces for up to, as much as, four weeks or more. When the insect pests track through, and come in contact with, previously sprayed product, the active ingredients remain on their bodies and they eventually die. Without the mineral oil, the composition dries, leaving no residue.

The concentrations of the active ingredients can be widely varied while producing a highly effective, non-poisonous, fast-acting, broad spectrum insecticide according to this invention. Formulations can incorporate from about 0.1% to about 20% by volume of cornmint oil and from about 0.01% to about 30% sodium lauryl sulfate, the remainder comprising inert ingredients such as water, mineral oil and/or a propellant. Preferred compositions include from about 2% to about 10% cornmint oil with about 0.1% to about 2% sodium lauryl sulfate.

Compositions containing 4% cornmint oil and 0.1% sodium lauryl sulfate have been found to be highly effective in killing flying insects, such as flies, mosquitoes, gnats, moths, yellow jackets and bees, as well as crawling insects such as ants, roaches, both German and American cockroaches, water bugs, silverfish, crickets, spiders and centipedes.

A preferred composition for general use comprises about 4% cornmint oil and about 1% sodium lauryl sulfate, the remainder being inert ingredients such as water, mineral oil, if desired, and a propellant such as carbon dioxide.

By increasing the concentration of the cornmint oil to, for example, about 8%, a more effective kill ratio is found for resistant flying insects such as wasps, hornets, yellow jackets and other bees. A composition of this nature can kill such targeted insect pests in a matter of seconds. Entire nests of such flying insects can be killed by spraying the aerosol into the nest opening until the nest is saturated.

Although the insecticidal composition of the instant invention is useful in an open, outdoor environment, it is also safe and effective for use indoors, even in a relatively confined area. The composition will not stain carpets or floors, is non-poisonous, and has a fresh mint scent.

Sodium lauryl sulfate alone does not kill the targeted insects. The cornmint oil itself does eventually kill at least some population of the targeted insect pests. However, the addition of sodium lauryl sulfate to the cornmint oil has been found to substantially reduce the kill time of all the targeted insect pests with which it came in contact. Moreover, the use of the synergistic combination of environmentally safe or nonpoisonous active ingredients of this invention has been found to kill targeted pests in a time generally equal to, or shorter than, commercially available insecticides which incorporated poisons.

To evidence the unexpectedly improved nature of the results obtained using the synergistic insecticidal composition of the instant invention, the following test protocol was established.

Scope

To determine the effectiveness of a nonpoisonous aerosol spray according to this invention as an insecticide when applied directly by a conventional pump spray[1] on German cockroaches, American cockroaches and various ant species.

[1] Comparisons to a commercial aerosolized poison-containing insecticide will be made in at least some tests.

Materials

Insects shall be healthy and undeformed. Only adult male and female insects shall be used for testing purposes. The insects shall be contained in a 21.5 in.×5.5 in.×5.5 in. testing arena.

Procedure

1. Gather 10 adult insects, 5 males and 5 females.
2. Place 1 insect into the testing arena.
3. Select spray to be tested. Spray cockroaches for 3 seconds, ants for 2 seconds.
4. Record kill time in seconds.
5. Wipe away any spray residue before beginning another test.
6. Repeat steps 2, 3, 4 and 5 until all test insects are used.
7. Record date of testing, type of test material used, type of insect used, kill time in seconds, and whether or not test specimen meets standard.

TABLE 1

The Effects of Cornmint Oil and Lauryl Sulfate on American Cockroaches

| Test No. | Active Ingredients (Volume %) | Kill Time (Seconds) |
| --- | --- | --- |
| 1. | 100% sodium lauryl sulfate (SLS) | 300[2] |
| 2. | 4% cornmint oil (CMO) 0% SLS | 300 |
| 3. | 4% CMO 1% SLS | 45.2 |
| 4. | 5% CMO 0% SLS | 300 |
| 5. | 5% CMO 1% SLS | 42.2 |
| 6. | 10% CMO 0% SLS | 300 |
| 7. | 10% CMO 1% SLS | 37.8 |

[2] An entry of 300 seconds in these Tables denotes that no deaths occurred during that time frame.

As seen from the above data and as graphically illustrated in FIG. 1, neither sodium lauryl sulfate alone (Test No. 1) nor cornmint oil alone (Test Nos. 2, 4 and 6), kills American cockroaches within the 300 second standard test time allotted. The addition of 1% sodium lauryl sulfate to a 4, 5 or 10% cornmint oil composition (Test Nos. 3, 5 and 7) show 100% effectiveness in killing the targeted insects. The above tests utilized the active ingredients in an aqueous solution dispensed from a standard pump-type sprayer. Shorter kill times result when the insecticide is aerosolized, i.e., dispensed from a pressurized aerosol can using a propellant such as carbon dioxide.

Thus, had the insecticidal compositions of this invention used in Test Nos. 3, 5 and 7 above been aerosolized, kill times of less than 45.2 sec., 42.2 sec. and 37.8 sec. would be expected. In contrast, comparison tests using an aerosolized bench-mark, commercially available insecticide incorporating active ingredients designated by the Environmental Protection Agency as poisons[3], averaged 197.2 seconds to kill American cockroaches.

[3] RAID® aerosol insecticide manufactured by S.C. Johnson, containing 0.2% pyrethrin, 0.2% permethrin and 0.5% piperonyl butoxide.

Thus, the combination of poison-free ingredients in the insecticidal composition of this invention effectively killed American cockroaches when the individual components were "not effective" and, did so in substantially less time than even a poison-containing commercial aerosol.

TABLE 2

The Effects of Cornmint Oil and Lauryl Sulfate on German Cockroaches

| Test No. | Active Ingredients (Volume %) | Kill Time (Seconds) |
| --- | --- | --- |
| 8. | 100% sodium lauryl sulfate (SLS) | 300 |
| 9. | 4% cornmint oil (CMO) 0% SLS | 76.4 |
| 10. | 4% CMO 1% SLS | 38.9 |
| 11. | 5% CMO 0% SLS | 39.8 |
| 12. | 5% CMO 1% SLS | 14.2 |
| 13. | 10% CMO 0% SLS | 30.2 |
| 14. | 10% CMO 1% SLS | 21.2 |

Figure 2:
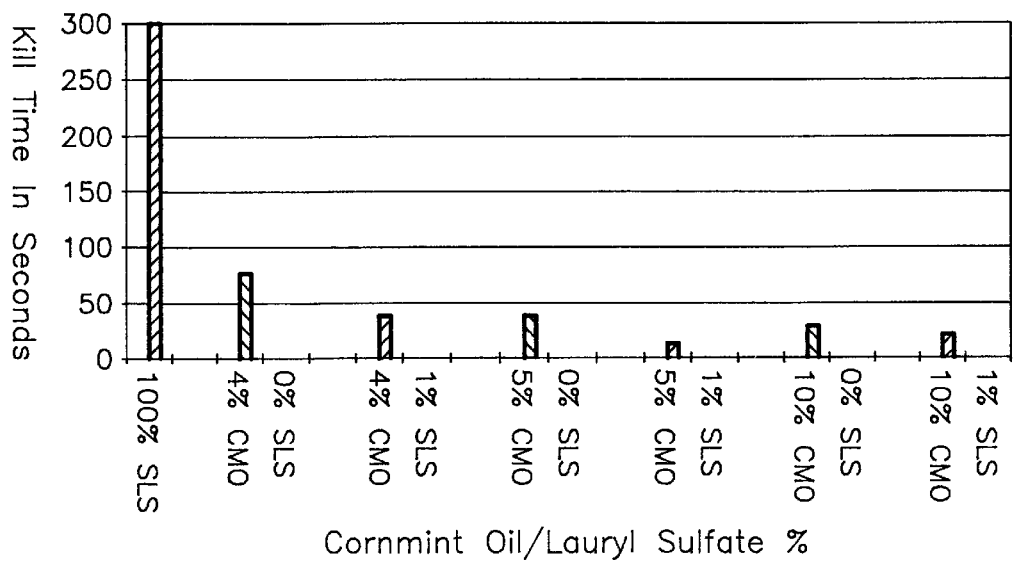
FIG. 2 is a bar graph illustrating the insecticidal effects of combining cornmint oil with sodium lauryl sulfate in killing German cockroaches.

Table 2 and FIG. 2 show that sodium lauryl sulfate alone is ineffective as an insecticide against German cockroaches (Test No. 8). Moreover, while cornmint oil alone shows some insecticidal activity (Test Nos. 9, 11 and 13), the addition of 1% sodium lauryl sulfate dramatically reduces the kill time (compare Test Nos. 10, 12 and 14).

The benchmark commercial poison-containing aerosol referred to above killed German cockroaches in an average of 19.2 seconds. An aerosolized 4% cornmint oil, 1% sodium lauryl sulfate composition according to this invention killed German cockroaches in about 21 seconds, without the need for environmentally undesirable poisons.

TABLE 3

The Effects of Cornmint Oil and Lauryl Sulfate on Black Ants

| Test No. | Active Ingredients (Volume %) | Kill Time (Seconds) |
| --- | --- | --- |
| 15. | 100% sodium lauryl sulfate (SLS) | 300 |
| 16. | 4% cornmint oil (CMO) 0% SLS | 87 |
| 17. | 4% CMO 1% SLS | 12.9 |
| 18. | 5% CMO 0% SLS | 72.9 |
| 19. | 5% CMO 1% SLS | 40.7 |
| 20. | 10% CMO 0% SLS | 49.4 |
| 21. | 10% CMO 1% SLS | 27 |

As seen from the data in Table 3, and as graphically illustrated in FIG. 3, similar unexpectedly reduced kill times are realized when the synergistic insecticidal composition of this invention is tested against black ants.

In summary, as will be seen from the foregoing test results, the individual components of the insecticidal composition of this invention, namely cornmint oil and sodium lauryl sulfate, are either ineffective, or relatively ineffective, in killing the targeted insect pests, whereas the combination of these materials unexpectedly killed substantially all insects contacted with the composition, and did so in a matter of seconds. For example, the addition of 1% sodium lauryl sulfate to 5% cornmint oil decreases the kill time of American cockroaches from "not effective" (over 300 seconds) to 42.2 seconds; the addition of 1% sodium lauryl sulfate to 5% cornmint oil decreases the kill time of German cockroaches from 39.8 seconds to 14.2 seconds; and the addition of 1% sodium lauryl sulfate to 4% cornmint oil decreases the kill time of black ants from 87 seconds to 12.9 seconds. Moreover, the kill time, as compared to a conventional aerosol insecticide incorporating poisonous active ingredients, was substantially the same or significantly reduced with the synergistic insecticidal composition of the instant invention.

Having described the invention, many modifications thereto will become apparent to those skilled in the art to which it pertains without deviation from the spirit of the invention as defined by the scope of the appended claims.

We claim:

1. An insecticidal composition comprising, as the essential active ingredient, a combination, in synergistic proportions, of about 2 to 10 percent by volume cornmint oil and about 0.1 to 30 percent by volume sodium lauryl sulfate.

2. The composition of claim 1 wherein said composition is in sprayable form and further comprises a propellant.

3. The composition of claim 2 wherein said propellant is carbon dioxide.

4. The composition of claim 1 further including mineral oil.

5. The composition of claim 1 comprising about 4 percent by volume cornmint oil and about 0.1 percent by volume sodium lauryl sulfate.

6. The composition of claim 1 comprising about 4 percent by volume cornmint oil and about 1 percent by volume sodium lauryl sulfate.

7. The composition of claim 1 comprising about 8 percent by volume cornmint oil and about 1 percent by volume sodium lauryl sulfate.

8. A method of controlling insect pests which comprises contacting the insect pests with an insecticidally effective amount of a composition according to claim 1.

9. A method of controlling crawling insect pests comprising contacting the insect pests with an insecticidally effective amount of a composition according to claim 4.

10. A method of controlling insect pests comprising contacting the insect pests with an insecticidally effective amount of a composition according to claim 5.

11. A method of controlling insect pests comprising contacting the insect pests with an insecticidally effective amount of a composition according to claim 7.

* * * * *